US007776914B2

(12) United States Patent
Spencer et al.

(10) Patent No.: US 7,776,914 B2
(45) Date of Patent: Aug. 17, 2010

(54) ESTERIFIED FATTY ACID COMPOSITION

(75) Inventors: William P. Spencer, Escondido, CA (US); Patrick S. Millsap, San Diego, CA (US)

(73) Assignee: Imagenetix, Inc., San Diego, CA (US)

( * ) Notice: Subject to any disclaimer, the term of this patent is extended or adjusted under 35 U.S.C. 154(b) by 0 days.

(21) Appl. No.: 12/485,865

(22) Filed: Jun. 16, 2009

(65) Prior Publication Data
US 2009/0252692 A1    Oct. 8, 2009

Related U.S. Application Data

(63) Continuation of application No. 10/805,386, filed on Mar. 22, 2004, now Pat. No. 7,612,111.

(51) Int. Cl.
  *A61K 31/19*    (2006.01)
(52) U.S. Cl. .................. 514/557; 514/547; 514/458; 514/560; 514/825; 514/900; 514/902; 424/769
(58) Field of Classification Search ........... 514/547, 514/557, 458, 560, 825, 900, 902; 424/769
  See application file for complete search history.

(56) References Cited

U.S. PATENT DOCUMENTS

| | | | |
|---|---|---|---|
| 4,113,881 | A | 9/1978 | Diehl |
| 4,330,557 | A | 5/1982 | Cavazza |
| 4,454,159 | A | 6/1984 | Musher |
| 5,569,676 | A | 10/1996 | Diehl |
| 6,417,227 | B1 | 7/2002 | Lord et al. |
| 2005/0208162 | A1 | 9/2005 | Spencer et al. |

FOREIGN PATENT DOCUMENTS

| | | |
|---|---|---|
| EP | 0 937 394 A | 8/1999 |
| JP | 64-30818 | 2/1989 |
| WO | 01/38288 | 5/2001 |
| WO | 01/85162 A1 | 11/2001 |

OTHER PUBLICATIONS

Diehl, H. W. et al. "Cetyl myrstoleate Isolated from Swiss Albino Mice: An Apparent Protective Agent Against Adjuvant Arthritis in Rats," J. Pharm. Sci., 1994, 296-99, 83(3), American Association of Pharmaceutical Scientists, Arlington, VA.

App. No. EP04757977 - Supplementary European Search Report issued Aug. 27, 2008.

Heasman, P. A. et al., "The Use of Topical Flurbiprofen as an Adjunct to Non-surgical Management of Periodontal Disease," J. Clin. Periodontol., 1993, 457-64, 20(6), John Wiley & Sons Ltd, Oxford, U.K.

Philstrom, B. L. et al., "Periodontal risk assessment, diagnosis and treatment planning," Periodontol. 2000, 2001, 37-58, 25.

Hasturk, H. et al., "1-Tetradecanol Complex Reduces Progression of Porphyromonas gingivalis-Induced Experimental Periodontis in Rabbits," J. Periodontol., 2007, 924-32, 78(5), American Academy of Periodontology, Chicago, IL.

Perneger, T. V. et al., "Risk of kidney Failure Associated with the Use of Acetaminophen, Aspirin, and Nonsteroidal Antiinflammatory Drugs," N. Engl. J. Med., 1994, 1675-79, 331(25), Massachusetts Medical Society, Boston, MA.

"Impact of Arthritis and Other Rheumatic Conditions," Morbidity and Mortality Weekly Report, 1999, 349-53, 48(17), Centers for Disease Control and Prevention, Atlanta, GA.

Wilcox, C. M. et al., "Striking Prevalence of Over-the-Counter Nonsteroidal Anti-inflammatory Drug Use in Patients with Upper Gastrointestinal Coverage," Arch. Intern. Med., 1994, 42-6, 154(1), American Medical Association, Chicago, IL.

Curtis, C. L. et al., "n-3 Fatty Acids Specifically Modulate Catabolic Factors Involved in Articular Cartilage Degradation," J. Biol. Chem., 2000, 721-724, 275(2), American Society for Biochemistry and Molecular Biology, Bethesda, MD.

Everts, B. et al., " Cox-2-Specific Inhibitors - the Emergence of a New Class of Analgesic and Anti-inflammatory Drugs", Clin. Rheumatol., 2000, 331-43, 19(5), Elsevier, Oxford, U.K. .

(Continued)

*Primary Examiner*—Deborah D Carr
(74) *Attorney, Agent, or Firm*—Sam K. Tahmassebi; TechLaw, LLP

(57) ABSTRACT

The invention is directed to compositions comprising lecithin, olive oil, esterified fatty acids and mixed tocophenols for use in the treatment and prevention of various types of arthritis and other inflammatory joint conditions, periodontal diseases and psoriasis, which avoid many of the side effects associated with known treatments. The compositions of the present invention have the advantage of increased stability, a reduction of arachidonic acid in cells, a reduction in eicosanoid production and enhanced cell regulation and communication. Also disclosed are methods for using the compositions for treatment and prevention.

20 Claims, No Drawings

OTHER PUBLICATIONS

Kremer, J. M. "Effects of Modulation of Inflammatory and Immune Parameters in Patients with Rheumatic and Inflammatory Disease Receiving Dietary Supplementation of n-3 and N-6 Fatty Acids", Lipids, 1996, 31 Supp: S243-S247, American Oil Chemists Society, Chicago, IL.

WO/2004/084829 - International Search Report dated Oct. 16, 2004 posted Jan. 27, 2005.

WO/2004/084829 - Written Opinion of International Searching Authority provided in the International Preliminary report on Patentability dated Sep. 23, 2005 and posted May 4, 2006.

Chem. Abst. of IT - 1302626, 2008.

Hasturk et al., "1-Tetradecanol Complex Reduces Progression of Porphyromonas gingivalis-Induced Experimental Periodontitis in Rabbits," Periodontol, 2007, vol. 78, No. 5, pp. 1-9.

ESTERIFIED FATTY ACID COMPOSITION

RELATED APPLICATIONS

The present application is a continuation of the U.S. application Ser. No. 10/805,386, filed Mar. 22, 2004 by William P. Spencer, et al. and entitled "ESTERIFIED FATTY ACID COMPOSITION," the entire disclosure of which is incorporated herein by reference, including any drawings.

FIELD OF THE INVENTION

The invention is directed to compositions comprising lecithin, olive oil, esterified fatty acids and mixed tocophenols for use in the treatment and prevention of various types of arthritis and other inflammatory joint conditions, periodontal diseases and psoriasis, which avoid many of the side effects associated with known treatments. The compositions of the present invention have the advantage of increased stability, a reduction of arachidonic acid in cells, a reduction in eicosanoid production and enhanced cell regulation and communication. Also disclosed are methods of using the compositions for treatment and prevention.

BACKGROUND OF THE DISCLOSURE

More than 400 million people around the world suffer from crippling, chronic pain caused by joint diseases, osteoporosis, spine disorders and musculoskeletal trauma. Osteoarthritis, the most common type of arthritis, affects more than 21 million Americans and is a leading cause of disability in the United States. By the year 2020, an estimated 60 million people in the U.S. will have some form of arthritis. Besides the physical toll, arthritis costs the U.S. nearly $65 billion annually. Arthritis is second only to heart disease as a cause of work disability. See MMWR (1999) 48:349-353.

Arthritis usually causes stiffness, pain and fatigue. In some people, only a few joints are affected and the impact may be small. In other people, the entire body system may be affected.

Known therapies for arthritis and inflammatory conditions are usually palliative and based on the use of analgesic or anti-inflammatory agents and physical modalities. Because anti-inflammatories (e.g., NSAIDS) confer potentially high risk for serious NSAID-induced gastrointestinal side effects and renal toxicity, therapies are needed that will be analgesic, anti-inflammatory, safe and favorably modify the disease history.

The newer class of NSAIDs (e.g. Vioxx™, Celebrex™) are based on the selective inhibition of COX-2. While COX-2 inhibitors have minimized gastrointestinal complications, they still maintain contraindications for congestive heart failure and renal dysfunction. See Wilcox et al., Arch. Intern. Med. (1994) 15:42-45; Perneger et al., N Eng J Med (1994) 331:1675-1679; and Everts et al., Clin. Rheumatol (2000) 19:331-43.

Thus, there is a serious need for an effective treatment and method of prevention of arthritis and other rheumatic and skeletal conditions that do not cause serious side effects. The present invention provides compositions and methods for treatment and prevention of arthritis and related conditions, while avoiding many of the problems associated with current treatments. These compositions have the further benefit of increased efficacy and stability and a reduction of arachidonic acid and eicosanoid production in cells.

SUMMARY OF THE INVENTION

The present invention is based on the discovery that the compositions of the present invention are effective in the treatment and prevention of arthritis and other inflammatory disorders but avoid certain side effects associated with known treatments, such as renal and cardiac dysfunction. These compositions have the added benefit of increased efficacy and stability, a reduction of arachidonic acid in cells, a reduction in eicosanoid production and enhanced cell regulation and communication. The present invention is also effective against psoriasis, lupus and heart/cardiovascular disease.

In one aspect, the invention is directed to a composition comprising a lecithin fatty acid, an olive oil fatty acid, an esterified fatty acid and mixed tocophenols.

The lecithin fatty acid may be about 1% to about 10% of the composition. Preferably, the lecithin fatty acid is about 1% to about 5% of the composition. More preferably, the lecithin fatty acid is about 5% of the composition. The olive oil fatty acid may be about 15% to about 25% of the composition. Preferably, the olive oil fatty acid is about 15% to about 20% of the composition. More preferably, the olive oil fatty acid is about 20% of the composition. The esterified fatty acid may be about 70% to about 80% of the composition. Preferably, the esterified fatty acid is about 70% to about 75% of the composition. More preferably, the esterified fatty acid is about 74% of the composition. The mixed tocophenols may be about 1% to about 5% of the composition. Preferably, the mixed tocophenols are about 1% to about 3% of the composition. More preferably, the mixed tocophenols are about 1% of the composition.

The lecithin fatty acid may include, but is not limited to, palmitic acid, stearic acid, palmitoleic acid, oleic acid, linoleic acid, linolenic acid and mixtures thereof. The olive oil fatty acid may include, but is not limited to, oleic acid, palmitic acid, linoleic acid, stearic acid, arachidic acid, and mixtures thereof. The esterified fatty acid may include, but is not limited to, decanoic acid, lauric acid, myristoleic acid, myristic acid, palmitoleic acid, palmitic acid, oleic acid, stearic acid and mixtures thereof.

In a further aspect, the invention is directed to a pharmaceutical composition for treating and/or preventing an arthritis or other inflammatory joint conditions, psoriasis, lupus, periodontal diseases or heart or cardiovascular condition comprising from about 1% to about 10% of a lecithin fatty acid, from about 15% to about 25% olive oil fatty acid, from about 70% to about 80% of an esterified fatty acid, and about 1% to about 5% of a tocophenol, and pharmaceutically appropriate carriers thereof. The pharmaceutical composition may further comprises biocompatible polymers as protective colloids, suspensions or bulking agents, excipients, binders and carriers, as appropriate.

In a further aspect, the invention is directed to a method of treating and/or preventing an arthritis or other inflammatory joint conditions, psoriasis, lupus, periodontal diseases or heart or cardiovascular condition comprising the administration of an effective amount of a composition comprising a lecithin fatty acid, an olive oil fatty acid, an esterified fatty acid and mixed tocophenols to a subject in need thereof. The arthritis or other inflammatory joint condition may include, but is not limited to, osteoarthritis, ankylosing spondylitis, cervical arthritis, firbromyalgia, osteonecrosis, Paget's Disease, bursitis, psoriasis, gout, carpal tunnel syndrome, juvenile rheumatoid arthritis, lumbosacral arthritis, psoriatic arthritis and rheumatoid arthritis. The subject may be a mammal. Preferably, the mammal is a human, canine or feline.

Preferably, the composition is administered topically. When administered topically, preferably the amount of the composition administered is about 1 to 15 mg/kg of body weight of said subject per day. More preferably, the amount of the composition administered is about 3 to 10 mg/kg of body weight of said subject per day. Most preferably, the amount of the composition administered is about 5 to 8 mg/kg of body weight of said subject per day.

The composition is also preferably administered orally. When administered orally, preferably the amount of the composition administered is about 5 to 32 mg/kg of body weight of said subject per day. More preferably, the amount of the composition administered is about 10 to 30 mg/kg of body weight of said subject per day. Most preferably, the amount of the composition administered is about 15 to 25 mg/kg of body weight of said subject per day. Preferably, the composition is administered orally via a soft gel, or alternatively, a tablet or capsule.

Preferably, the composition may be administered once a day or twice a day.

In a further aspect, the invention is directed to a method wherein the composition is administered to a subject in combination with another compound or therapy effective to treat or prevent arthritis or other inflammatory joint conditions, psoriasis, periodontal diseases, lupus or cardiovascular and heart disease.

DETAILED DESCRIPTION OF THE EMBODIMENTS

In general, the terms in the present application are used consistently with the manner in which those terms are understood in the art.

By the term "arthritis and other inflammatory joint conditions," as used herein, is meant joint inflammation, and refers to more than 100 different diseases, including, but not limited to, osteoarthritis, ankylosing spondylitis, cervical arthritis, firbromyalgia, osteonecrosis, Paget's Disease, bursitis, psoriasis, gout, carpal tunnel syndrome, juvenile rheumatoid arthritis, lumbosacral arthritis, psoriatic arthritis and rheumatoid arthritis. These diseases usually affect the area in or around joints, such as muscles and tendons. Some of these diseases can also affect other parts of the body, including the skin and internal organs.

By the term "topically" is meant application over the afflicted area. For example, the present invention may be applied over the knee joint, or anywhere on the body in order to put the composition into the blood stream.

By the term "periodontal diseases" is meant any inflammatory condition resulting in the destruction of the support structure of the dentition.

A. Compositions and Methods of Treatment and Prevention Using Same

The present invention is directed to a composition that is particularly effective in the treatment and prevention of arthritis and other inflammatory joint conditions, as well as psoriasis.

The inflammation process of arthritis involves the release of pro-inflammatory cytokines (e.g., IL-1β and TNF-α). Fatty acids have been shown to affect these inflammatory cytokines in patients with rheumatoid arthritis. It is likely that dietary supplements of these fatty acids reduce chronic inflammation of rheumatoid arthritis by reducing the release of leukotriene B4 from stimulated neutrophils and of interleukin-1 from monocytes.

Esterified fatty acids (EFA) are fatty acids esterified to cetyl alcohol that are found in small amounts in ruminant fat reported that rats injected with EFA showed greatly increased resistance to adjuvant-induced arthritis. Recently, osteoarthritis patients given EFA showed significant improvement in quality of life. Thus, EFA has potent physiological effects. See Curtis et al, J. Biol Chem (2000) 275:721-724; and Kremer, Lipids (1996) 31 Supp:5243-47.

Esterified fatty acids (EFA) are well absorbed when given orally or topically. Most of the EFA are metabolized, with only a small proportion remaining intact in the tissues or plasma. EFA and its metabolites distribute to various tissues, such as liver, kidney, muscle, and adipose tissue. The lipid profile of EFA and its metabolites in tissues is similar between oral and topical administration. The largest proportion of intact EFA are found in the skin tissue at the site of topical administration.

Thus, the present invention uses an esterified fatty acid formulation. The present formulations are composed of lecithin fatty acids, olive oil fatty acids and esterified fatty acids. The formulations may also contain mixed tocophenols. Preferably, the formulations comprise 5% lecithin, 20% olive oil, 74% esterified fatty acids and 1% mixed tocophenols.

In addition to being effective against arthritis and other inflammatory conditions, the ingredients of the compositions confer other advantages. Specifically, the mixed tocophenols, as a liquid antioxidant, provide the advantage of increased efficacy, stability and preservation to the fatty acid blend. The fatty acid carbons cause a reduction of arachidonic acid in cells, a reduction in eicosanoid production via lipoxygenase and cyclooxygenase and enhanced cell regulation and communication. Tables 1-3 below provide preferred lecithin fatty acids, olive oil fatty acids and esterified fatty acids for use in the present invention.

TABLE 1

Lecithin fatty acids

| Carbons | Acid Name | Typical % |
| --- | --- | --- |
| C16:0 | palmitic acid | 11% |
| C18:0 | stearic acid | 4% |
| C16:1 | palmitoleic acid | 8% |
| C18:1 | oleic acid | 10% |
| C18:2 | linoleic acid | 57% |
| C18:3 | linolenic acid | 4% |
| C20-C22 | various acids | 6% |

TABLE 2

Olive Oil fatty acids

| Carbons | Acid Name | Typical % |
| --- | --- | --- |
| C18:1 | oleic acid | 84% |
| C16:0 | palmitic acid | 9% |
| C18:2 | linoleic acid | 4% |
| C18:0 | stearic acid | 2% |
| C20:0 | arachidic acid | 1% |

TABLE 3

Esterified fatty acids

| Carbons | Acid Name | Typical % | acid molecular weight | esterified fatty acid molecular weight |
|---|---|---|---|---|
| C10:0 | decanoic acid | 1% | 172 | 396 |
| C12:0 | lauric acid | 1% | 200 | 424 |
| C14:1 | myristoleic acid | 25% | 226 | 450 |
| C14:0 | myristic acid | 40% | 228 | 452 |
| C16:1 | palmitoleic acid | 7% | 254 | 478 |
| C16:0 | palmitic acid | 5% | 256 | 480 |
| C18:1 | oleic acid | 20% | 282 | 506 |
| C18:0 | stearic acid | 1% | 284 | 508 |

The most preferred formula blend of the present invention is shown in Table 4

TABLE 4

Preferred formulation blend

| Compound | Typical % |
|---|---|
| lecithin | 5% |
| olive oil | 20% |
| esterified fatty acids | 74% |
| mixed tocophenols | 1% |

The present invention, whether taken orally or topically, delivers a group of compounds that are found in limited supply in the normal diet. The primary components not consumed in large amounts are cetyl alcohol and the carbon 14 fatty esters, myristic acid and myristoleate.

These compounds are distributed within the various tissues. The resulting chylomicrons are then distributed within the circulation and made available to the entire cellular matrix. In addition, it is very likely that with both oral and topical use, there is probably some distribution within tissue spaces prior to the first pass through the liver. One likely pathway is the adipocytokine pathway recently found within the body. The primary compound in this pathway is leptin. Leptin is considered to be involved in the inflammatory process both as an initiator and as a down regulator.

Fatty acid products can induce alterations in the cellular membrane. Monounsaturated fatty acids similar to those found in the present invention have been shown to inhibit endothelial activation and to reduce tissue responsiveness to cytokines. Fatty acids have been shown to regulate a variety of enzymatic processes that regulate chronic inflammatory disease.

Arachidonic acid is one of the primary mediators for inflammation. Fatty acids from fish oil have been shown to decrease the amount of arachidonic acid in cell membranes reducing eicosanoid production via cyclooxygenase and lipoxygenase. It is the integration between arachidonic acid byproducts and their involvement with leukotriene and proglandins that lead to inflammation control. The fatty acids within the present invention work to limit eicosanoid production thereby reducing the inflammatory cascade.

There is evidence showing that fatty acids have profound impact on cellular regulation and communication. The primary organs for this process are the endoplasmic reticulum and Golgi body apparatus. These two cellular structures are the main manufacturers of the cellular signals within the body. The immediate benefit found with the present invention is such rapid cellular communication and regulation.

One area that has great potential is the interplay between the fatty acid compounds of the present invention and sphingolipids. Sphingolipids are essential for cellular function and are uniquely integrated with the endoplasmic reticulum and Golgi bodies. Sphingolipids are considered dynamic regulators of cellular processes. The variable structure of sphingolipids and glycerolipids trigger the formation of microdomains or rafts within the membrane. Spingolipids are traditionally based upon a C18 fatty acid backbone, but over 60 different species are known with chain lengths varying from 14 to 20 carbons differing in saturation and hydroxylation.

The influence of dietary manipulation of sphingolipids and glycerolipids in vitro has demonstrated that stearic acid and EPA can alter the endoplasmic reticulum to Golgi body lipid trafficking compared to oleic acid. One result was an inhibition of ER lipid synthesis and transfer of membrane lipids to luminal particles. In addition, the polyunsaturated fatty acid mediation of T cell inhibition is attributable to signal protein displacement in membranes. The alteration in lipid rafts is the primary loci.

The formulation content can be adjusted for pH and isotonicity as needed, as understood by the skilled artisan. Preferably, the pH range is 4.0 to 8.0. These formulations can also include biocompatible polymers such as polyvinyl pyrrolidone (PVP), polyvinyl alcohol (PVA) or polyethylene glycol (PEG), and other polymers as protective colloids and suspension or bulking agents, excipients, binders and carriers, as appropriate.

Well known oral dosage forms that work well with the present invention include pills, tablets, including coated tablets, capsules, gel capsules, soft gels, elixirs, emulsions, micro-emulsions and pre-emulsion concentrates for controlled or immediate release. Soft gels are the most preferred oral form. Solubility plays a large role in the development of oral dosage formulations, because the formulation used to deliver the active drug will affect the amount and/or concentration of the drug that reaches the active site over a given period of time. The composition of the formulation also directly affects the solubilization of the drug compound in the gastrointestinal tract, and consequently the extent and rate of the absorption of the active drug compound into the blood stream. In addition, the therapeutic value of a drug is affected by the rate in which the drug is released from the delivery system itself, which in turn affects the rate and extent of solubilization of the active compound in the gastrointestinal tract before absorption.

In addition to effectively treating arthritis or other inflammatory joint conditions, periodontal disease, psoriasis, lupus or cardiovascular and heart disease, the compositions of the present invention are effective at preventing these conditions. In the same way that fatty acids work within the cell to reduce inflammation, they also work within the cell to prevent inflammation from reoccurring. Further, the compositions of the present invention, by reducing and preventing inflammation, prevent the onset of diseases and conditions which result from inflammation. For example, by reducing inflammation of the arteries, the compositions of the present invention prevent occurrences of heart disease and cardiovascular disease.

The appropriate dosage of the composition of the present invention will depend, for example, on the condition to be treated/prevented, the severity and course of the condition, whether the composition is administered for preventive or therapeutic purposes, previous therapy, the patient's clinical history and response to the composition and the discretion of the attending physician.

Preferably, the composition is administered topically. When administered topically, preferably the amount of the composition administered is about 1 to 15 mg/kg of body weight of said subject per day. More preferably, the amount of the composition administered is about 3 to 10 mg/kg of body weight of said subject per day. Most preferably, the amount of the composition administered is about 5 to 8 mg/kg of body weight of said subject per day. When administered orally, preferably the amount of the composition administered is about 5 to 32 mg/kg of body weight of said subject per day. More preferably, the amount of the composition administered is about 10 to 30 mg/kg of body weight of said subject per day. Most preferably, the amount of the composition administered is about 15 to 25 mg/kg of body weight of said subject per day.

The composition is suitably administered to the patient at one time or over a series of treatments, and may be administered to the patient at any time from diagnosis onwards. The composition may be administered as the sole treatment or in conjunction with other drugs or therapies useful in treating and preventing the condition in question.

Thus, in practicing the methods of this invention, the compounds of this invention may be used alone or in combination with other therapeutic agents. As used herein, two (or more) agents are said to be administered in combination when the two agents are administered simultaneously or are administered independently in a fashion such that the agents will act contemporaneously. In certain preferred embodiments, the compositions of this invention may be co-administered along with other treatments typically prescribed for these conditions according to generally accepted medical practice. For example, the compositions of this invention can be administered in combination with other therapeutic agents or physical therapies for the treatment and/or prevention of arthritis or related conditions. Some of the conditions contemplated for treatment with the present invention, either alone or in combination with other known therapies, are provided below. Typical therapies are also provided, which may be administered in combination with the present invention.

Rheumatoid arthritis is characterized by inflammation of the peripheral joints, potentially resulting in progressive destruction of articular and periarticular structures, with or without generalized manifestations. Treatments include NSAIDs, salicylates, gold compounds, cytotoxic or immunosuppressive drugs and corticosteroids.

Ankylosing spondylitis (AS) is categorized as a type of seronegative spondyloarthropathies. Neurologic and cardiological signs can occasionally result. AS is characterized by mild or moderate flares of active spondylitis alternating with periods of almost or totally inactive inflammation. Treatment includes daily exercise, NSAIDs and corticosteroids, which have limited therapeutic value.

Osteoarthritis includes marked thickening and proliferation of the anterior longitudinal ligaments. Functional compromise of the vertebral arteries, infarction of the spinal cord, and esophageal compression by osteophytes occasionally occur. Treatment includes acetaminophen or NSAIDs, and may include surgeries such as laminectomy, osteotomy, and total joint replacement.

A vascular necrosis occurs in the femoral and humeral heads, the body of the talus, and the carpal scaphoid. Post-traumatic avascular necrosis develops when blood supply is impaired and is thus a function of the relative contributions of arteries to the femoral or humeral head and the extent of anastomoses between them, which varies among persons. Treatment includes analgesics, range-of-motion exercise and cortical bone grafts.

Acute infectious arthritis is caused by bacteria or viruses. *Neisseria gonorrhoeae* is the most common bacterial cause in adults. It spreads from infected mucosal surfaces (i.e., cervix, rectum, pharynx) to the small joints of the hands, wrists, elbows, knees and ankles. Chronic infectious arthritis is caused by mycobacteria, fungi, and some bacteria with low pathogenicity. Treatment includes antibiotics.

Acute gouty arthritis (gout) may be precipitated by minor trauma, overindulgence in purine-rich food or alcohol, surgery, fatigue, emotional stress, or medical stress (e.g., infection, vascular occlusion). The pain becomes progressively more severe and is often excruciating. Treatments include NSAIDs, colchicine, and lowering the urate concentration in extracellular body fluid.

Osteochondromatosis is characterized by numerous cartilaginous loose bodies in a swollen, painful joint. Surgery is needed to remove the loose bodies along with the synovium of the joint.

Osteoporosis occurs when the amount of bone available for mechanical support of the skeleton eventually falls below the fracture threshold, and the patient may sustain a fracture with little or no trauma. The major clinical manifestations of osteoporosis are bone fractures, which cause chronic pain. Treatment includes pharmaceuticals, maintenance of adequate body weight, increased walking and other weight-bearing exercises.

Paget's disease is characterized by increased bone density, abnormal architecture, cortical thickening, bowing, and overgrowth. Treatment may include salicylates, NSAIDs, orthotics and orthopedic surgery.

Dystonias are sustained muscle contractions that can lead to repetitive twisting movements and abnormal postures. Torticollis is a chronic, focal dystonia that is different from wryneck, an active, painful, self-limited neck spasm. Treatment includes intensive physical therapy, anticholinergics and benzodiazepines.

Boutonniere Deformity (Buttonhole Deformity) is caused by disruption of the central slip attachment base of the middle phalanx extensor tendon, creating a so-called buttonholing of the proximal phalanx between the lateral bands of the extensor tendon. Surgical reconstruction after fixed deformities develop is often found to be unsatisfactory.

Dupuytren's Contracture (Palmar Fibromatosis) is progressive contracture of the palmarfascial bands, producing flexion deformities of the fingers. Treatment includes local injection of a corticosteroid suspension into the nodule, surgery and high-dose vitamin E.

Carpal Tunnel Syndrome is the term used to describe a specific group of symptoms (tingling, numbness, weakness, or pain) in the fingers or hand and occasionally in the lower arm and elbow. These symptoms occur when there is pressure on a nerve within the wrist. Treatment often includes surgery.

Sports injuries include lateral and medial epicondylitis (tennis elbow) and patellofemoral pain (runner's knee). The most common cause of muscle or joint injury is overuse. Treatment for almost all acute athletic injuries includes ice, compression and elevation, as well as local corticosteroid injections.

Psoriasis is characterized by skin cells that multiply up to 10 times faster than normal. As underlying cells reach the skin's surface and die, their sheer volume causes raised, red patches covered with white scales. Treatment includes, salicylic acid and steroids.

Lupus is an autoimmune disease that can cause inflammation, pain, and tissue damage throughout the body. Treatment includes anti-inflammatory medications.

Cardiovascular and heart disease is often characterized by inflammatory lesions throughout the vascular system. Reducing the inflammation of the vascular system can reduce the risk and/or severity of heart/cardiovascular disease.

Periodontal diseases are comprised of a group of inflammatory conditions that result in the destruction of the supporting structure of the dentition, caused by hyperactivated inflammatory conditions. The activated condition causes the release of toxic compounds which degrade the surrounding dentition. The regulation of these toxic compounds is similar to compounds found in most inflammatory conditions derived from cell membrane oxidation and/or tissue phospholipid liberation. Fatty acids modulate the inflammatory cascade via leukotriene, prostaglandin and thromboxane pathways.

Treatments of periodontal disease includes oral rinse and gum gels containing tetracycline, chlorhexidine, doxycycline and minocycline. It is believed that antibiotic intervention reduces or eliminates the viability of gram-negative and anaerobic bacteria commonly found in the mouth cavity. Elimination of the bacterial load retards the development of periodontal disease and bone loss. Oral administration of fatty oils elicits a reduction in gingival inflammation. The topical application of the compositions and formulations of the present invention can accomplish similar reductions in bacterial load.

Example 1

Bioavailability of EFA Complex

An in vitro experiment was conducted using an esterified fatty acid (EFA) complex, to determine the bioavailability of the complex in acidic and enzymatic systems replicating stomach and intestinal contents. An aliquot of the complex was subjected to a pH of 2.0 and to pancreatic lipase. The experiment showed negligible amounts of breakdown during either the low pH or lipase action.

In addition to this in vitro work, rats adapted to a purified diet were fed meals containing 2% of the EFA or no EFA. Two hours later, stomach and small intestine contents were collected and the intestinal mucosa scrapped. Lipids were extracted, separated by hydrolysis and evaluated by the presence of cetyl alcohol. In rats fed a meal without EFA, no cetyl alcohol or EFA was found in any sample. In EFA-fed rats, no cetyl alcohol was found in the stomach or intestinal contents or in the mucosa, indicating no hydrolysis. However, EFA was found within the mucosa, demonstrating absorption.

To further elucidate on the EFA complex bioavailability, the base fatty acid material was cetylated with a labeled cetyl alcohol. The product was purified and fed to rats normalized on a purified diet. The stomach, intestinal and mucosa contents were again analyzed for hydrolytic by-products. The results demonstrate that about 40% of the EFA complex was hydrolyzed into cetyl alcohol and fatty acids. It was determined that stomach and intestinal contents, primarily the fat load, determine the amount of hydrolysis of the EFA complex.

Safety of EFA Complex

An oral toxicity study was conducted. Rats were given about 1 teaspoon of the esterified fatty acid complex [via oral gavage]. The results of the experiment demonstrated that a dose equal to 1300 times that given to humans elicited no changes in rat behavior and general health, as well as any abnormalities determined via histology of the major organs (e.g., heart, kidney and liver).

A study was conducted to determine whether the esterified fatty acids in topical cream form induced skin rash or irritation after application for up to 140 days. Nude mice were used. After 140 days of application, the topical ream did not induce skin rash or irritation, nor did it induce any histological changes in the underlying epidermis.

Efficacy of EFA Complex

The oral soft gel was tested. Subjects were given soft gels daily (6 per day) for a total of 68 days. The two main outcome variables were knee range of motion and response on the Lequesne Algofunctional Index. Subjects on the active esterified fatty acid oil increased their knee range of motion by about 10 degrees that was statistically significant from the placebo group. In addition, probability estimates from the Lequesne Index indicated that active participants achieved statistically significant ability in their functional independence.

Example 2

The topical cream was studied. Fourteen subjects suffering from psoriasis were given a cream, three of which received a placebo. Evaluation at 7 and 14 days showed improvement in pruritis (itching) and a lessening of psoriasis. The cream also provided improvement in scaling, redness, skin cracking, and inflammation.

Example 3

Distribution of Esterified Fatty Acid in Rats after Oral or Topical Administration It was the objective of this study to determine the intestinal and topical absorption of esterified fatty acids (EFA), its tissue distribution, and its metabolic form after absorption. Male Wistar rats (10) were divided into two groups. Both groups were fed a standard rodent purified diet (AIN-93G). One group of five rats was gavaged twice daily with 220,000 DPM of 14C-labelled esterified fatty acids. To the other group of five rats, 220,000 DPM of 14C-labelled esterified fatty acids was applied topically twice a day to an area of shaved skin between the shoulders. The fatty acid mixture used in the synthesis contained various fatty acids, but was enriched in myristoleic acid (25%). After seven days of treatment, the animals were anesthetized with ethyl ether, blood was removed by cardiac puncture, and liver, kidney, and sample of muscle tissue from the hind leg were collected, weighed, and frozen. In addition, a two-day fecal collection was made in the last two days of the experiment.

Lipids were extracted from plasma, tissue samples and feces, spotted on to thin layer chromatography plates, and separated into lipid classes. Lipid classes were visualized by exposure to iodine vapor, marked, scraped into liquid scintillation vials, and counted. Apparent intestinal absorption was estimated by determining fecal excretion and subtracting that from intake, expressed as a percent of intake. Intestinal absorption was virtually complete. Thus, when taken orally, EFA are absorbed to the same high degree as dietary triglycerides.

The distribution of the radiolabel within a tissue was similar regardless of whether the radiolabel was administered orally or topically. In each tissue examined, the majority of radiolabel was found in phospholipids or triglycerides. The one exception to this finding was in adipose tissue from topically applied radiolabel; in this case, a significant amount of radiolabel was found in the fraction of an unknown lipid.

The amount of radiolabel present as intact EFA was relatively small in each tissue examined. The amount was greatest in liver, where is occurred as approximately 6-7% of the radiolabel, and least in kidney and adipose, where it varied from <1% to 2%.

In the distribution of radiolabel in the small intestinal mucosa of rats given the radiolabel orally, the vast majority of radiolabel was present in the phospholipid fraction, with little as intact EFA (approximately 1%).

The plasma radiolabel distribution among lipid fractions was similar in both orally and topically administered animals. Again, the majority of radiolabel was found in the triglyceride and phospholipid fractions. Relatively little intact EFA was present. In both the perirenal fat pad and kidney, the amount of radiolabel present was similar for both the orally and topically administered rats. However, in the liver, there was much more radiolabel present from animals given the radiolabel orally than topically. This would be consistent with oral ingestion, as lipids absorbed from the diet are taken up to a high degree by the liver prior to redistribution to other organs.

The profile of radiolabeled lipids in the plasma was similar between rats treated orally or topically. Consistent with the findings in tissues, the majority of the radiolabel was found in the triglyceride and phospholipid fractions. Only a relatively small amount of radiolabel was found in the EFA fraction. Thus, regardless of the mode of administration, EFA appear to be secreted into plasma primarily as fatty acid esters (e.g., triglycerides, phospholipids, cholesterol esters).

At the site of topical administration, there remained a significant proportion of radiolabel in the EFA form. However, considerable radiolabel appears in the triglyceride fraction, with lesser amounts in phospholipids and cholesterol esters. There was also a large amount of radiolabel in the unknown lipid fraction.

This study, using a radiolabeled form of esterified fatty acids (EFA), demonstrates that EFA are absorbed when administered either orally or topically. Intestinal absorption appears to be essentially complete. Based on the similar amounts of radioactivity in adipose and kidney, it is likely that topically absorption is also nearly complete.

From the distribution of the radiolabel amongst the various lipid fraction, it is clear that most EFA are metabolized, with only a small quantity of EFA remaining intact within the tissues and plasma. In the synthesis of the radiolabeled EFA, radiolabeled cetyl alcohol was used, so the cetyl alcohol contained the radioactive carbon.

Based on the appearance of radiolabel in the TLC fraction corresponding to cetyl alcohol, it is clear that the EFA are being hydrolyzed to cetyl alcohol and fatty acids. Further, the finding of radiolabel in fractions corresponding to phospholipid, triglyceride, and cholesterol ester, indicates that the cetyl alcohol was oxidized to palmitic acid (and probably subsequently to other fatty acids). The palmitic acid was then esterified into phospholipids, triglycerides, and cholesterol esters.

The tissue with the greatest proportion of intact EFA was the liver. This proportion was similar between the oral and topical treatments. This suggests that the liver may be the major site of EFA metabolism i.e., the hydrolysis and subsequent oxidation to fatty acids of the cetyl alcohol occurs largely in the liver, with subsequent export of the fatty acids, as triglyceride.

With topical application, considerable EFA remains in its intact form within the skin. However, even here, there is significant metabolism of EFA into fatty acid, with incorporation into triglyceride, phospholipid, and cholesterol ester. Therefore, the liver may not be the only site of metabolism.

Thus, esterified fatty acids are well absorbed when given either orally or topically. Although a small proportion of esterified fatty acids remain intact, the vast majority is hydrolyzed and the cetyl alcohol is oxidized to fatty acids and esterified into various types of lipids (e.g., phospholipids, triglycerides, and cholesterol esters).

Example 4

The purpose of this investigation was to examine the effects of using a topical cream consisting of esterified fatty acids on pain and functional performance in patients diagnosed with osteoarthritis (OA) of one or both knees. Forty-two patients, 35 women and 7 men, diagnosed with knee OA were matched and randomly assigned to 1 of 2 topical treatment groups: 1) esterified fatty acid (CMC) (N=21; age=61.9±11.9 yrs); or 2) placebo (P) group (N=21; age=64.9±10.5 yrs). Patients were tested on 3 occasions: 1) baseline (T1) period prior to cream treatment, 2) then after 3 days without treatment, participants applied an initial treatment to the affected areas and the outcome measures were obtained after 30 mm of application (T2), and 3) following a 30-day treatment period consisting of cream application twice per day (T3).

Assessments included knee range of motion (ROM), 40-sec standing center of pressure (COP) on a force plate to measure postural sway, timed up-and-go from a chair, timed stair climbing ability (up and down steps), and the single-leg anterior reach (a measure of unilateral strength and balance). Test-retest reliabilities for all tests ranged from 0.95 to 0.99. For stair climbing ability and the up-and-go tests, significant decreases in time were observed at T2 (−1.39 and −0.66 sec, respectively) and T3 (−1.78 and −1.03 sec, respectively) compared to T1 in CMC only. These differences were significant between groups ($P<0.001$). A significant reduction (−0.07 m) was observed for movement of COP during a 40 sec and standing test in CMC only. Supine ROM of the knees increased at T2 and T3 in CMC, whereas no differences were observed in the P group. In the single-leg anterior reach, significant improvements were observed for both legs in CMC and only the left leg in the P group. However, the improvements observed in CMC were significantly greater than the P group for both legs (5.1 and 4.4 cm versus 0.8 and 1.8 cm respectively for the right and left legs). These results indicate that the use of a topical cream containing esterified fatty acids is an effective treatment for reducing pain and improving physical function in patients with OA. Specifically, patients with OA had significantly greater ROM of the knee in the supine extended and flexed knee positions, less standing postural sway, improved ability to ascend and descend stairs, improved ability to rise from sitting, walking, and sitting down, and greater unilateral balance.

Example 5

The effect of a esterified fatty acids for improving the quality of life of canines was studied. This study investigated whether esterified fatty acids (EFA) could improve the quality of life (QOL) in arthritic canines. Small and large breed dogs were enlisted in the study regardless of current arthritic medication.

Animals were recruited from a veterinary practice in a suburb of San Diego, Calif. The vet clinic had a sizeable number of canines currently under care for the treatment of joint health disease. The owners read and signed an informed consent. The study was conducted using animal care guidelines for veterinary practices.

The owners were instructed to bring the dog in for an assessment by the veterinarian. Upon enrollment, the owner completed a medical history and general Quality of Life (QOL) survey. During this time the veterinarian gave the pet a physical exam of major body areas and joint structures, which is standard for musculoskeletal disease assessment. Blood and urine were collected with each visit. The dog was given a 30-day supply of EFA product. The owners were also told to take their dogs on daily walks lasting from 10 to 20 minutes. The animals were maintained on their current medication regimen. The owner then returned with the pet after 30 days for the final physical assessment by the veterinarian and to fill out the QOL survey again.

Esterified Fatty Acid Product

The animal was given dog chews containing a mixture of EFA, dextrates, desiccated liver and hickory flavor. A standard dose of two chews per day per 20 pounds was established.

Quality of Life Survey and Analysis

The survey was filled out at the initial visit and again after 30 days of supplementation. The owners were asked to write their answers next to the questions.

Clinical Measures

These measures were taken at the initial visit and again after 30 days of supplementation. Each dog had blood drawn from the jugular vein with a 22-gauge needle attached to a 6 cc syringe. This is standard practice to minimize any pain and anxiety the animal might experience in having it's blood drawn. Experienced, licensed registered veterinary technicians drew the blood. The blood was placed in a lavender top tube and a serum separator tube. The blood in the serum separator tube was allowed to clot (10 minutes) then spun in a centrifuge. Both tubes were placed in the clinical reference laboratory bag (IDEXX Veterinary Services, Inc. Atlanta, Ga.). The appropriate forms were filled out and then the entire bag was placed in the refrigerator for transport to the clinical reference laboratory. A standard chemistry 27 panel was obtained plus a comprehensive CBC.

Urine was obtained by using an ultrasound probe to locate the bladder then by performing ultrasound-guided cystocentesis or by walking the dog and collecting a "free catch" sample into a sterile collection container. The urine obtained by either method was placed into a red top tube (no serum separator gel was used) and placed in the IDEXX bag for collection. The appropriate forms were filled out for the laboratory and placed in the bag with the urine and the blood. Standard urine biomarkers were obtained for each collection.

Clinical Analysis

Clinical chemistry tests were performed on Hitachi 747-200® chemistry auto-analyzers using wet reagents. After calibration, normal and abnormal controls were run before each testing sequence, after every 50 specimens, and again, after each run sequence to ensure calibration stability. Quality commercial reagents used were standard to the equipment.

Hematology tests were performed on Abbott Cell-Dyne® 3500 auto-analyzers using the laser flow cytometry methodology. Hematology results were verified by several different means including commercial controls, patient controls, pre-assayed standard calibration samples, machine-to-machine comparisons and inter-laboratory comparisons and controls run on every shift.

A total of 27 animals were enrolled in the study, 24 animals completed the study. There were two animals dropped from the study due to noncompliance. One animal was euthanized due to complications unrelated to the study protocol. Average demographics of the dogs were as follows: Age (yrs) =10.5±2.0; Weight (lbs)=70.4±25.0; and Gender (male/female)=13/11.

The average length of time on the study product was 32.8±5.7 days.

There were no changes in serum or urine biomarkers after the 30 day supplementation period. There were a few animals that had some modest improvement in their gait, but over the clinical evaluation did not uncover any noticeable improvements.

The owners' responses to the questionnaire provided some enlightening information. Owner comments for the QOL survey were very favorable. Each owner was also asked to write in their own words what they felt was achieved with the dietary intervention. There was a consistent pattern among participants for improved vitality and function.

The present study demonstrated the benefit of using an EFA supplement as an intervention in the treatment of canines with musculoskeletal conditions. The animals exhibited typical signs and symptoms of degenerative joint disease or osteoarthritis. It is worth noting that many animals were currently on a standard prescription for treating their malady but were still able to experience improvement. The present study investigated the use of esterified fatty acids for improving QOL in canines of various breeds. The pet owners felt that their animals had improved mobility and energy compared to their observations prior to the intervention. While clinical examination did not reveal any noticeable differences, it is not uncommon for dogs to "stiffen" when being evaluated. This serves as a protective mechanism when confronted in unfamiliar environments.

In summary, esterified fatty acids improved the general disposition and functional ability in dogs suffering from arthritis. These fatty acids offer an alternative to more traditional therapies for treating arthritis in canines.

TABLE 5

Clinical biomarkers obtained from serum and urine samples

| Biomarker | Delta Changes |
| --- | --- |
| White blood cells | 0.12 ± 1.8 |
| Neutrophil segmentation | −0.42 ± 11.7 |
| Platelets | −23.12 ± 165.4 |
| Absolute Neutrophils | 187.0 ± 1872.2 |
| Alkaline phosphate | −15.4 ± 76.7 |
| SGPT (ALT) | −1.12 ± 39.6 |
| SGOT (AST) | 0.08 ± 5.5 |

TABLE 6

Quality of Life Questionnaire Response by Owner

| Symptom (Question #)* | # Dogs with symptom | % of Dog Improving |
| --- | --- | --- |
| Difficulty Rising | 18 | 44% |
| Up or Down Stairs | 17 | 47% |
| Sit or Lag on Walks | 10 | 70% |
| Move Slowly/Stiffly | 13 | 54% |
| Pain During/After Walks | 11 | 64% |
| Limping on Walks | 13 | 69% |
| Reduce Stride Length | 7 | 43% |
| Limping | 15 | 67% |
| Difficulty Sitting Down | 5 | 80% |
| Rear Legs Collapse | 8 | 50% |

*These are the symptoms with more than 40% improvement.

TABLE 7

Most Common Owner Comments

| Comment Type* | Number |
| --- | --- |
| General Improvement | 10 |
| Improvement in Wanting to Play, Move, Exercise | 10 |
| Improvement in Walking, Limping | 9 |
| Improvement in Attitude, Temperament, Energy | 7 |
| Likes/Wants Supplement | 5 |

*Voluntary written comments by owners

Example 6

Periodontitis is a local inflammation that occurs as a result of host response against specific microorganisms and eventually leads to tissue destruction and systemic complications. The cause of this infectious disease is specific Gram-negative microorganisms, such as *Porphyromonas gingivalis* and *Bacteriodes forsythus*. While the etiology of periodontitis is bacterial, it is clear that the pathogenesis is mediated by the host response.

It has been reported that monosaturated fatty acids inhibit endothelial activation and reduce tissue responsiveness to cytokines. Fatty acids have been shown to regulate a variety of enzymatic process that regulates chronic inflammatory disease. In addition, it has also been shown that fatty acids can decrease the amount of arachidonic acid in cell membranes, reducing eicosanoids production via cyclooxygenase and lipoxygenase. It is the integration between arachidonic acid byproducts and their involvement with leukotriene and prostoglandins that lead to inflammation control. These mechanisms play an important role in the development of periodontal inflammation. Moreover, high epithelial penetration ability of fatty acids through gingival epithelium suggests that the local application may be favorable in the treatment of periodontal inflammation.

Rabbits represent a useful model, in which the physiology and the pathology of periodontal tissues resemble that of humans with respect to the pro-inflammatory and anti-inflammatory mechanisms. A predictable and reproducible periodontitis can be generated in rabbits by using silk ligatures accompanied by the topical application of periodontitis-specific microorganism *P. gingivalis*.

The aim of the study is to investigate the topical application of a monosaturated fatty acid complex (Genepril™) on ligature-induced periodontitis model in rabbits. For this purpose, an already well-established model of periodontitis in rabbit jaws will be used, placing silk ligatures around the second premolars with topical application of the periodontitis-specific pathogen *Porphyromonas gingivalis*. While the first group of animals (test group) will topically receive the fatty acid complex formulated medication, the second group (control group) will receive vehicle alone. After the animals are sacrificed at 6 weeks, histological and radiographical evaluations of tissue specimens will be made. The results of this study will be used to understand the local effects of cetylated fatty acids on the gingival tissues and periodontal disease progression.

Experimental Design

A total of 10 male New-Zealand White rabbits will be equilibrated and housed. On the day of the experiment, rabbits will be anesthetized using xylazine (subcutaneous, 0.25 mL) and ketamine (40 mg/kg, IM) and if necessary intubated and given isoflurane (1-2.5 MAC). A ligature (3-0 braided silk suture) will be placed around the second premolars of both sides of the mandible. Every other day (Monday, Wednesday and, Friday), animals will be anesthetized using isoflurane to apply the topical medications around the ligatures.

*P. gingivalis* (strain A7436), grown using standard procedures at 109 CFU mixed with carboxy methyl cellulose to form a thick slurry, will be applied topically to the ligated teeth to induce periodontitis. Following the *P. gingivalis* application, a test agent or placebo will be applied topically to the same areas for six weeks. At these times, the sutures will also be checked, and lost or loose sutures will be replaced. Ethanol will be used as solvent for fatty acid complex.

At the end of the six weeks, animals will be euthanized by Pentobarbital overdose (100+ mg/kg, IV). After euthanasia, the mandible of each rabbit will be dissected free of muscles and soft tissue, keeping the attached gingiva intact with the alveolar bone. The mandible will be split into two halves from the midline between the central incisors. The left half will be taken for morphometric analysis of the bone and the right half will be used for histological evaluation of the use of the test and placebo agents in periodontitis. It is expected that the topical application of a monosaturated fatty acid complex on ligature-induced periodontitis model in rabbits will have a positive effect in reducing, treating the periodontitis.

The potential effects of the monosaturated fatty acid complex (cetylated fatty acids) in the prevention of the periodontal inflammation induced by the periodontitis-specific microorganism *P. gingivalis* will be studied. Experiments will be performed on 10 rabbits for duration of 6 weeks. For most of the histological studies, 5-6 animals per group will be sufficient to show the differences between groups in a $p<0.05$ statistical significance. Because there will be two groups in this study: 1) Test agent group, and 2) Placebo group, 5 animals per group will be appropriate for this study (1 test group and 1 placebo group×4 animals/group=10 animals).

It is expected that the monosaturated fatty acid complex (cetylated fatty acids) will have a positive effect in the prevention of the periodontal inflammation induced by *P. gingivalis*.

While this invention has been particularly shown and described with references to preferred embodiments thereof, it will be understood by those skilled in the art that various changes in form and details may be made therein without departing from the spirit and scope of the invention as defined by the appended claims.

All references discussed above are herein incorporated by reference in their entirety.

What is claimed is:

1. A method of treating periodontal disease comprising administering an effective amount of a composition comprising a cetylated fatty acid to a subject in need of such treatment, wherein the cetylated fatty acid is selected from the group consisting of cetylated decanoic acid, cetylated lauric acid, cetylated myristic acid, cetylated palmitoleic acid, cetylated oleic acid, and cetylated stearic acid.

2. The method of claim 1, wherein the subject is a mammal.

3. The method of claim 2, wherein the mammal is human.

4. The method of claim 2, wherein the mammal is canine or feline.

5. The method of claim 1, wherein the composition is administered via topical application.

6. The method of claim 5, wherein the amount of the composition administered is about 1 to 15 mg/kg of body weight of said subject per day.

7. The method of claim 5, wherein the amount of the composition administered is about 3 to 10 mg/kg of body weight of said subject per day.

8. The method of claim 5, wherein the amount of the composition administered is about 5 to 8 mg/kg of body weight of said subject per day.

9. The method of claim 1, wherein the composition is administered orally.

10. The method of claim 9, wherein the amount of the composition administered is about 5 to 32 mg/kg of body weight of said subject per day.

11. The method of claim 9, wherein the amount of the composition administered is about 10 to 30 mg/kg of body weight of said subject per day.

12. The method of claim 9, wherein the amount of the composition administered is about 15 to 25 mg/kg of body weight of said subject per day.

13. The method of claim 9, wherein the composition is administered via a soft gel.

14. The method of claim 1, wherein the composition is administered once a day.

15. The method of claim 1, wherein the composition is administered twice a day.

16. The method of claim 1, wherein the cetylated fatty acid is cetylated myristic acid.

17. A method of treating periodontal disease comprising administering an effective amount of a composition comprising cetylated myristic acid to a subject in need of such treatment.

18. The method of claim 17, wherein the composition is administered via topical application.

19. The method of claim 18, wherein the amount of the composition administered is about 5 to 8 mg/kg of body weight of said subject per day.

20. A method of treating periodontal disease comprising topically administering an effective amount of a composition comprising cetylated myristic acid to a subject in need of such treatment, wherein the amount of the composition administered is about 5 to 8 mg/kg of body weight of said subject per day.

* * * * *